(12) United States Patent
Adams et al.

(10) Patent No.: US 6,549,279 B2
(45) Date of Patent: Apr. 15, 2003

(54) METHOD AND APPARATUS FOR OPTICAL ENDPOINT CALIBRATION IN CMP

(75) Inventors: John A. Adams, Escondido, CA (US); Robert A. Eaton, Scottsdale, AZ (US); Charles Chen, Sunnyvale, CA (US)

(73) Assignee: SpeedFam-IPEC Corporation, Chandler, AZ (US)

( * ) Notice: Subject to any disclaimer, the term of this patent is extended or adjusted under 35 U.S.C. 154(b) by 94 days.

(21) Appl. No.: 09/829,493

(22) Filed: Apr. 9, 2001

(65) Prior Publication Data

US 2003/0020909 A1 Jan. 30, 2003

(51) Int. Cl.[7] .................................................. G01J 3/28
(52) U.S. Cl. ........................ 356/326; 356/308; 356/330; 356/362; 356/419
(58) Field of Search ................................ 356/368, 328, 356/419, 362, 330

(56) References Cited

U.S. PATENT DOCUMENTS

| | | | | |
|---|---|---|---|---|
| 3,885,879 A | * | 5/1975 | Louder et al. | 250/227.28 |
| 4,193,691 A | * | 3/1980 | Fjarlie | 349/201 |
| 4,732,476 A | * | 3/1988 | Barshad | 356/308 |
| 4,886,341 A | * | 12/1989 | Oishi et al. | 356/328 |
| 5,565,983 A | * | 10/1996 | Barnard | 356/328 |
| 5,570,180 A | * | 10/1996 | Nagai | 356/310 |

* cited by examiner

Primary Examiner—Michael G. Lee
Assistant Examiner—Seung Ho Lee
(74) Attorney, Agent, or Firm—Snell & Wilmer, L.L.P.

(57) ABSTRACT

The invention provides calibrated spectrometers in a multi-spectrometer system, where chemical mechanical polishing endpoint detection is an issue. In one aspect of the invention, a spectrometer is calibrated by selecting a filter slide having a predetermined light transmittance or reflectance variation with location (e.g. angular or linear displacement) on the slide. Light is incident on locations on the filter slide, and this incidence light is either transmitted or reflected. Transmitted or reflected light is received by a spectrometer, and the wavelength measured is compared with the known wavelength that corresponds to its location on the slide. The spectrometer is calibrated by normalizing the wavelength readings obtained at various locations on the slide with the known readings dictated by the reference slide. The spectrometers are also calibrated to a standard light source for intensity of light. During polishing of workpieces, each spectrometer monitors surface spectral data, and converts these via its unique normalization factors to normalized values that are then compared with the normalized stored spectral data from the test piece. Once measured data (after normalization) approaches the endpoint set for the test piece within a predetermined degree of difference the endpoint of CMP has been reached and polishing may be manually or automatically terminated.

33 Claims, 12 Drawing Sheets

METHOD AND APPARATUS FOR OPTICAL ENDPOINT CALIBRATION IN CMP

BACKGROUND OF THE INVENTION

1. Field of the Invention

This invention relates to chemical mechanical polishing, used in a variety of technologies to produce planarized surfaces and to polish thin films, and in particular to the semiconductor wafer industry. More particularly, the invention relates to the detection of an endpoint for the polishing process using optical endpoint detection apparatus, and the calibration of these apparatus.

2. Description of the Related Art

Chemical mechanical polishing (CMP) has emerged as a critical technology in the manufacture of electronic devices on semiconductor wafers, particularly for the fabrication of devices that have critical dimensions smaller than 0.5 microns. CMP is used at various stages in the fabrication of semiconductor electronic devices on semiconductor wafers, and is generally used to either remove excess material deposited on the wafer surface, or to planarize the wafer surface, or both. The removal of excess material at various points in the process is necessary to produce the electrical interconnects required in the completed device. Also, planarization at various points in the process is necessary to ensure accurate and precise development of the structure of the electronic devices being fabricated in the wafer surface.

An important aspect of CMP is endpoint detection (EPD). Endpoint detection is the determination of when to terminate polishing. Many users prefer EPD systems that are "in-situ", that predict or detect the endpoint during the polishing process.

One of the techniques for EPD is the use of optical systems. For example, an optical EPD system is disclosed in U.S. Pat. No. 5,433,651. In this patent, an optical fiber carrying a light signal transmits the signal through a window in the platen of a rotating CMP tool to interrogate the wafer surface and a reflected optical signal is analyzed to determine whether the endpoint has been reached.

Another approach entails monitoring absorption of particular wavelengths of the infrared spectrum of a light beam incident on the rear side (i.e. side not being polished) of a wafer that is being polished. Thus, the beam passes through the wafer from the non-polish side of the wafer to the other side to detect a thin film on the surface being polished. Changes in the absorption of infrared light, within narrow well-defined spectral windows, correspond to changing thickness of specific types of films on the wafer surface being polishing. An example of this approach is disclosed in U.S. Pat. No. 5,643,046.

In general, in a semiconductor fabrication facility ("fab") a plurality of spectrometers will be used if optical EPD is the method of detecting endpoint. At least one spectrometer would be associated with each CMP tool. In these systems, a light source generally provides light through a optical fiber to the surface of a wafer. Light that is either reflected from or transmitted through the wafer is received in a second fiber, and transmitted to a spectrometer, where the light is channeled into various components based on wavelength. As received from vendors, the wavelength per channel and the linearity of the wavelength per channel is generally not always identical from one spectrometer to another within the same fab and the degree of variation poses limitations. Thus, for example, spectrometers are not generally interchangeable within a fab, and may not accurately predict endpoint if they are so interchanged. Further, if the fab uses a technique that permits the spectrometer to compare input light with stored data from a standard wafer, then each spectrometer would have to be calibrated separately, and differently, for that standard wafer.

SUMMARY OF THE INVENTION

This summary of the invention section is intended to introduce the reader to aspects of the invention and is not a complete description of the invention. Particular aspects of the invention are pointed out in other sections hereinbelow and the invention is set forth in the appended claims, which alone demarcate its scope.

The invention provides calibrated spectrometers in a multi-spectrometer system, such as found in a fab, that are each configured with respect to wavelength and light intensity for the optical detection of endpoint during chemical mechanical polishing of semiconductor wafers, flat panel displays, lenses, and other workpieces that undergo polishing where endpoint detection is an issue.

In one aspect of the invention, a spectrometer is calibrated by selecting a filter slide having a predetermined light transmittance or reflectance variation with location (e.g. angular or linear displacement) on the slide. Light is incident on locations on the filter slide, and this incident light is either transmitted or reflected. Transmitted or reflected light is received by a spectrometer, and the wavelength measured is compared with the known wavelength that corresponds to its location on the slide. The spectrometer is calibrated by normalizing the wavelength readings obtained at various locations on the slide with the known readings dictated by the reference slide. This normalizing may be carried out by any of a number of mathematical techniques, some of which are discussed herein. A similar normalization technique is also carried out for light intensity reading normalization, in accordance with the invention.

When all spectrometers in a multi-spectrometer system have been calibrated using the normalization techniques of the invention for wavelength and intensity, then a single test workpiece may be polished, and continuously optically monitored during polishing with any one of the calibrated spectrometers. Spectral measurements obtained from the monitoring are normalized, using the same normalization function/factors used in the calibration of the spectrometer. The endpoint for polishing may be determined based on the normalized data, and the normalized endpoint spectral signature in terms of wavelength and intensity may be determined. This normalized information may then be digitally stored and utilized on any of the other spectrometers for endpoint detection, since each of these have been normalized (by its own unique normalization factors) to a common standard for both wavelength and intensity. Absent such normalization, each spectrometer might have to be calibrated by polishing a test workpiece for each spectrometer separately and continuously monitoring that test workpiece during polishing to develop a spectral signature for endpoint determination.

During polishing of workpieces, each spectrometer monitors surface spectral data, and converts these via its unique normalization factors to normalized values that are then compared with the normalized stored spectral data from the test piece. Once measured data (after normalization) approaches the endpoint set for the test piece within a predetermined degree of difference the endpoint of CMP has been reached and polishing may be manually or automatically terminated.

Thus, the invention eliminates the need for the polishing of large numbers of test workpieces for instrument calibration, and permits the potential interchangeability of one spectrometer for another, in a multi-spectrometer system, without need for further recalibration.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings which are schematic and not to scale, wherein.

DETAILED DESCRIPTION OF THE PREFERRED EMBODIMENT

Figure 1:
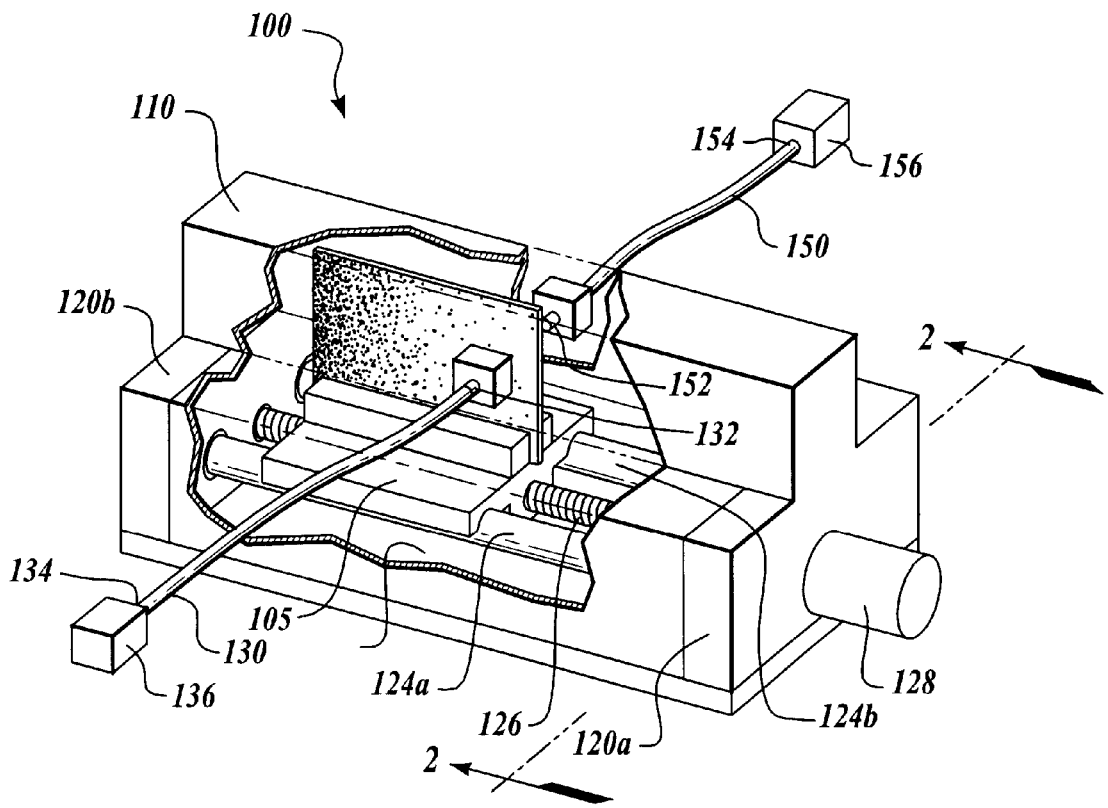
FIG. 1 is a schematic representation of a partial cutaway perspective view of an embodiment of a device in accordance with the invention showing a filter slide mounted to a calibration table, with light input from a source, and transmitted light output to a spectrometer.

This section illustrates aspects of the invention, and points out certain preferred embodiments of these aspects. This section is not intended to be exhaustive, but rather to inform and teach the person of skill in the art who will come to appreciate more fully other aspects, equivalents, and possibilities presented by invention, and hence the scope of the invention as set for the in the claims, which alone limit its scope.

The invention provides several advantages in an environment that utilizes multiple optical instruments for taking measurements and making determinations regarding processes and products. In particular, the invention finds application in those manufacturing industries where a plurality of spectrometers are used to measure the optical properties of a workpiece undergoing manufacture, such as in a semiconductor fabrication facility ("fab") where silicon wafers are processed to produce semiconductor chips and where chemical mechanical polishing (CMP) is used to polish and planarize semiconductor wafers during the process. In a fab, spectrometers are used to monitor polishing and planarizing of wafers during CMP, and to predict or detect the endpoint of the polishing process. Obviously, the techniques taught in this invention are also useful in processes to produce flat panel displays, optical lenses, memory disks, and the like.

In accordance with one embodiment of the invention, spectrometers in a multi-spectrometer environment are calibrated through normalization for wavelength and light intensity, at least, to a common "standard". As a consequence, in a fab environment, only one test semiconductor wafer need be polished to calibrate all of the spectrometers effectively for endpoint detection. Further, the calibration techniques of the invention potentially permit interchangeability of one spectrometer for another, without need to further recalibrate the replacement instrument.

When all spectrometers in a multi-spectrometer system have been calibrated using the normalization techniques of the invention for wavelength and intensity, then a single test workpiece may be polished, and continuously optically monitored during polishing with any one of the calibrated spectrometers. Measurements obtained from monitoring are normalized, using the same normalization function/factors used in the calibration of the spectrometer. The endpoint for polishing may be determined based on the normalized data, and the normalized endpoint spectral signature in terms of wavelength and intensity may be determined. This normalized information may then be stored and utilized on any of the other spectrometers for endpoint detection, since each of these have been normalized (by its own unique normalization factors) to a common standard for both wavelength and intensity. Absent such normalization, each spectrometer might have to be calibrated by polishing a test workpiece for each spectrometer separately and continuously monitoring that test workpiece during polishing to develop a spectral signature for endpoint determination.

During polishing of workpieces, each spectrometer monitors surface spectral data, and converts these via its unique normalization factors to normalized values that are then compare with the normalized spectral data from the test piece. Once measured data (after normalization) approaches the endpoint set for the test piece within a predetermined degree of difference the endpoint of CMP has been reached and polishing may be manually or automatically terminated.

In order to better appreciate some embodiments of the invention, a few non-limiting examples will first be described.

Figure 2:
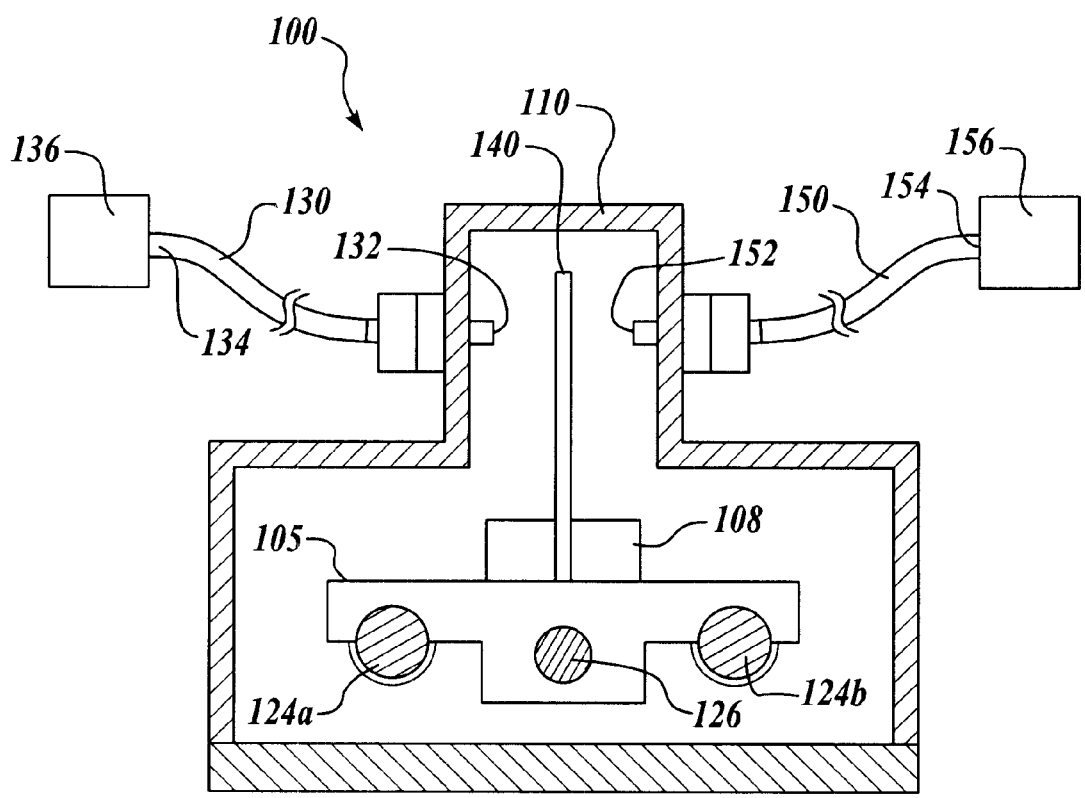
FIG. 2 is an end view of the device of FIG. 1, shown in cross-section taken at 2—2.

FIG. 1 is a perspective partial cut away view of an embodiment of the optical calibration tool of the invention and FIG. 2 is a cross-sectional end view of this embodiment. The calibration instrument is contained within a housing 110, seen more clearly in cross-section in FIG. 2. This housing provides a light tight fit over the instrument. In this example, the calibration tool 100 includes a precision linear screw-driven table with base 105, to which is mounted a pair of end blocks 120a and 120b. These end blocks hold a pair of parallel bearing rails 124a and 124b, a precision screw 126, and the screw movement mechanism 128. The precision screw 126 is coupled to the table 105 and moves the table linearly along the bearing rails 124a and 124b. A filter slide 140 is mounted to a mounting block 108 that is in turn mounted to the table 105. Thus, rotating the screw movement mechanism 128 causes the filter slide 140 to move linearly and in a controlled fashion along the length of the optical calibration tool 100.

The screw movement mechanism 128 may be any device that allows controlled rotation of the precision screw 126. Thus, the mechanism may be a micrometer head attached to screw 126 so that direct readings of table 105 movement may be obtained as screw 126 is rotated. Alternatively, the screw movement mechanism may be a motor and encoder so that the movement of the table 105 may be performed under computer control.

As shown in FIG. 1, optical endpoint light source 136 transmits light along optical input fiber 130, that has an output end 132 in close proximity to the filter slide 140 and an input end 134. Likewise, the optical endpoint detector assembly 156 receives light transmitted through the filter slide 140 via output fiber optic cable 150. Fiber optic cable 150 has an input end 152 located on an opposite side of the filter slide 140 from the output end 132 of the optical input cable 130, such that the two ends 132 and 152 register with each other and light transmitted from cable 130 enters cable 150.

Figure 12:
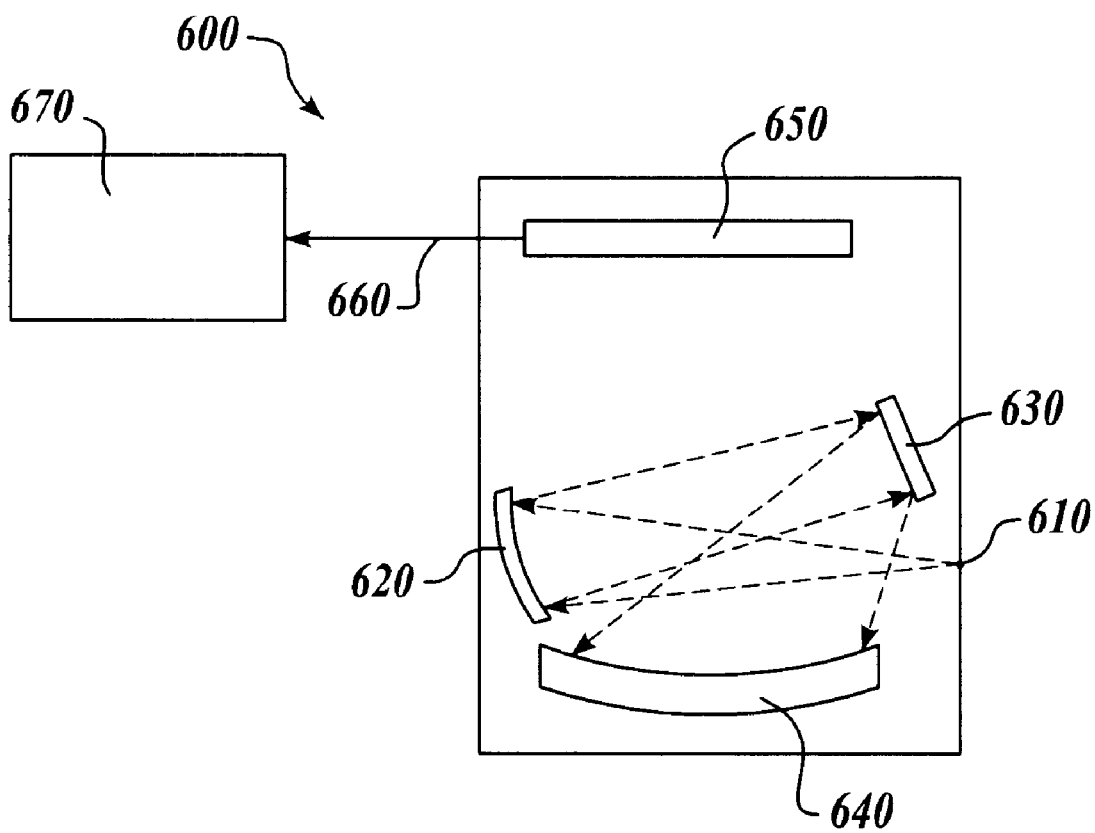
FIG. 12 illustrates schematically the internals of a spectrometer.

The optical endpoint detector assembly 156, is similar to the S2000 Miniature Fiber Optic Spectrometer from Ocean Optics, Dunedin, Fla. FIG. 12 illustrates details within assembly 156. Light is depicted entering a light tight spectrometer head 600 at location 610 and diverges as shown by the straight-dashed arrows onto a first curved front surface mirror 620, onward to a second mirror 630 and falls onto a curved grating 640. The grating 640 splits the wavelengths of light present in the input into a spatial difference as is known in the art. The spatially separated wavelengths of light fall onto a linear CCD detector 650 which is a one-dimensional linear CCD array, and the data is transferred to a computer 670 through electrical connection 660 and into an A/D card (not shown) where the intensity is digitized for each channel in the CCD. Thus intensity vs. CCD channel number is obtained within digital memory within the computer as a measure of the input light to the spectrometer. The operation of digital spectrometers is well known in the art. A factory calibration of wavelength vs. channel number is typically performed by the vendor of the spectrometer. The following equation, EQ. 1, is typically used:

$$\lambda_{ch}=C_0+(C_1*ch)+(C_2*ch*ch)+(C_3*ch*ch*ch) \quad (EQ.1)$$

Where:

$\lambda_{ch}$=wavelength in nanometers (nm) of channel number (ch) in the CCD $C_0$=wavelength of channel number zero (0)

$C_1$=$1^{st}$ coefficient (nm/ch)

$C_2$=$2^{nd}$ coefficient (nm/ch$^2$)

$C_3$=3rd coefficient (nm/ch$^3$)

ch=channel number in the CCD (typically range from zero to 2047)

These coefficients must be determined fairly frequently if the calibration of the spectrometer is to be maintained and if the results of one spectrometer are to be compared to another.

In one example, the filter slide 140 may be a Schott Veril linear interference slide, with transmittance that varies linearly across the glass substrate (Model H45645 from Edmund Scientific, Barrington, N.J.). This type of slide has a linear variation of about 7 nm per mm of length, and a spectral range of about 400 to about 700 nm. The filter's peak transmittance is about 40 percent, and typical bandwidth is about 15 nm.

Using the apparatus of FIGS. 1 and 2, the filter 140 is moved horizontally under control of screw movement mechanism 128 so that various narrow bandwidths of transmission are moved past the ends of the optical fibers 132 and 152. This transmitted bandwidth is a function of both the filter bandwidth, and additional bandwidth due to the spreading of the light onto the filter from optical fiber 130, and the angular acceptance of the transmitted light by the output fiber 150.

Clearly, other slides can be used in place of the Schott Veril slide referenced above. For example, a transparent colored slide may be used. By moving the slide controlledly horizontally, a variety of spectral signatures may be presented to the spectrometer for calibration purposes.

In a further embodiment, the ends of the optical fibers 152 and 132 may be arranged to view the colored slide or filter through expanding lenses, so that a wider range of wavelengths is present in the spectrum to be used for testing.

Figure 11:
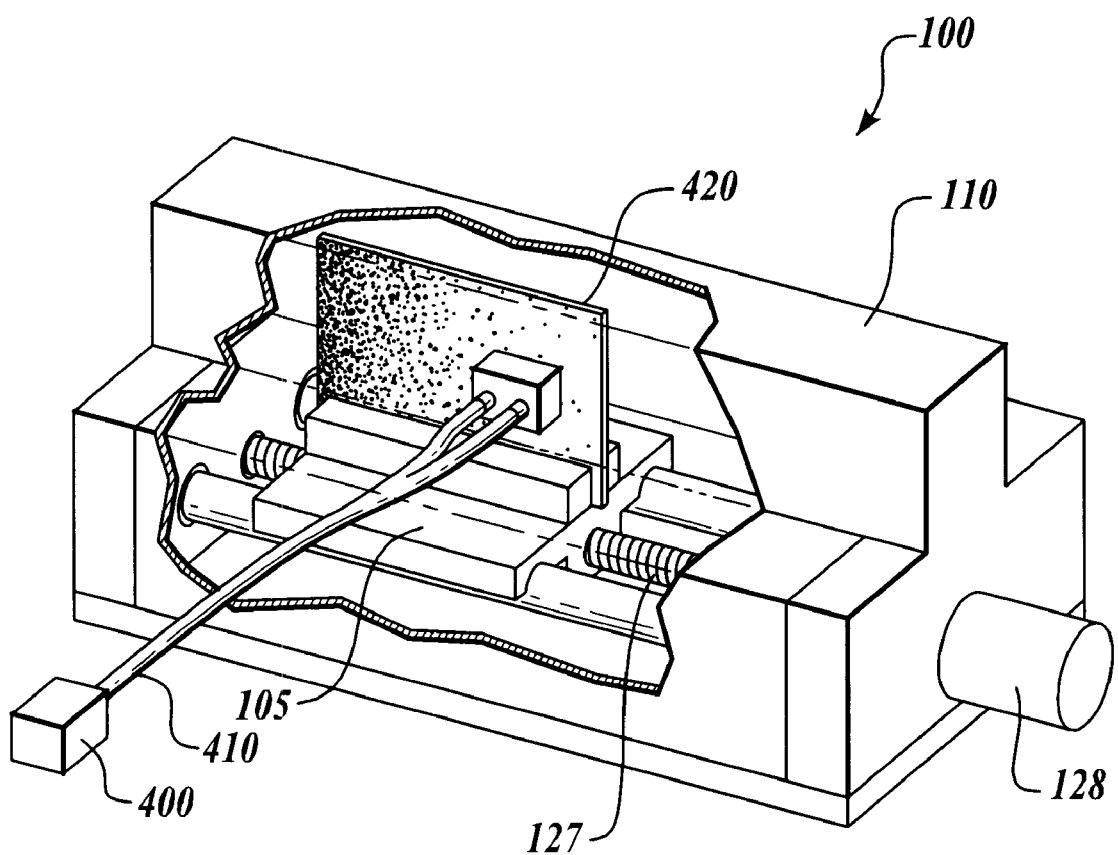
FIG. 11 is an embodiment of the invention similar to the embodiment of FIG. 1, but with a reflectance slide mounted to a calibration table, and with a bifurcated fiber optic cable.

In a further embodiment, instead of the optical fibers facing opposite sides of a "transmission type" filter, both fibers may view the same side of a reflectance slide, or the reflectance surface may be viewed with a bifurcated fiber, or by directly illuminating the reflectance slide and viewing it with the detector directly. Such an alternative embodiment is shown in FIG. 11. In this embodiment, light from the light source 400 is transmitted along a bifurcated optical fiber 410, although the fiber need not be bifurcated. Light from the source impinges on the reflectance slide 420, and is reflected back into the optical fiber and transported to a light detector 400. The reflectance slide, like the light transmittance slide discussed above, has a predetermined variation of reflected light wavelength with displacement along the length of the slide.

Figure 3:
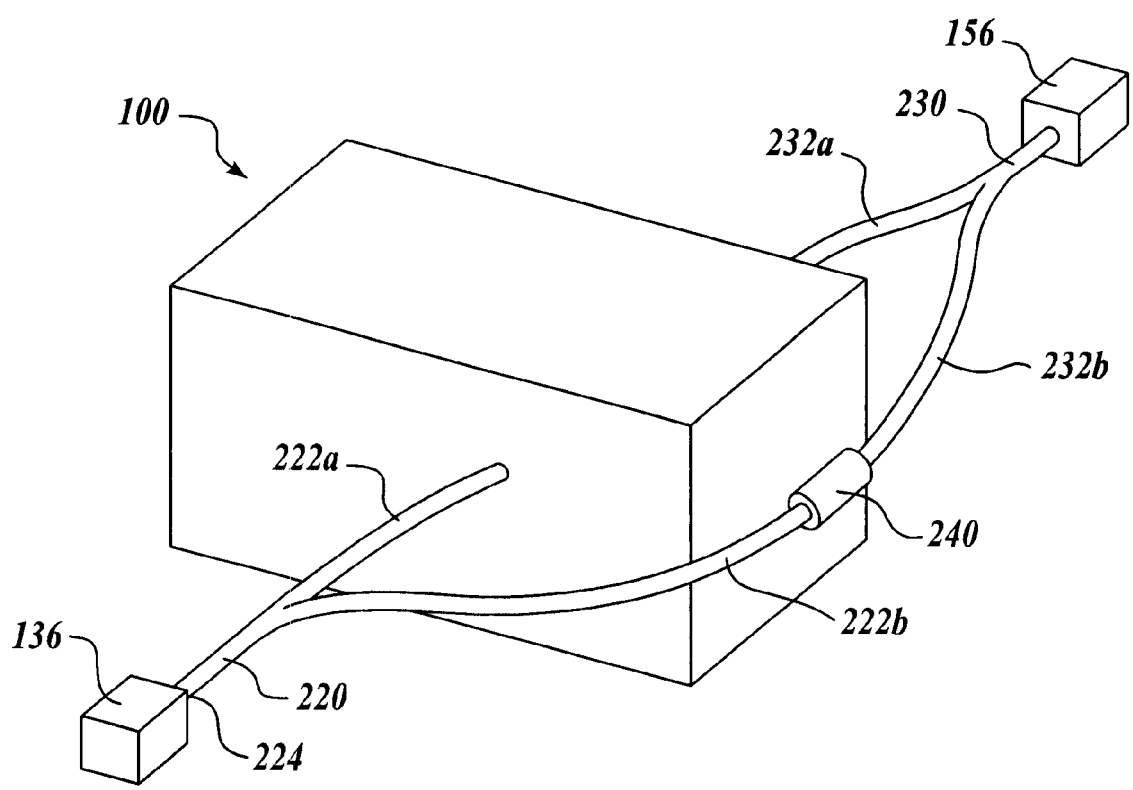
FIG. 3 is another embodiment of an apparatus in accordance with the invention, using bifurcated optical fibers.

FIG. 3 illustrates an embodiment in accordance with the invention that utilizes bifurcated optical fiber. The details of optical calibration instrument 100 explained with reference to FIGS. 1 and 2, are omitted for the sake of brevity and the instrument is shown as a "black box". As shown, light source 136 is connected to a bifurcated light input optical fiber 220, through one of the legs of the fiber 224. The other two legs of the input optical fiber 220 extend outward in a Y formation with one end 222a extending into the optical calibration tool 100, and the other end 222b bypassing the tool 100. Likewise, the optical detector 156 is also connected to a bifurcated output optical fiber 230, with one leg 232a extending into the calibration tool 100, and the other leg 232b bypassing the calibration tool to connect with the bypass end 222b of the input cable 220 through coupler 240.

When the apparatus of FIG. 3 is in use, light from the optical source 136 travels both through the optical calibration tool 100 to the optical detector 156, as well as around the tool directly to the optical detector 156 through legs 222b and 232b. By varying the light transmission efficiency of the bifurcated optical cables, the percentage of total light delivered to the detector 156 from the calibration tool 100 or directly from the light source 136 can be varied. This dual optical path allows testing of the system with a small modulation on the spectrum from the light source to simulate the small modulation that is ordinarily present when measuring thin transparent films on semiconductor wafers. This feature can also be achieved by placing an attenuation filter in one of both optical paths.

In the embodiment illustrated in FIG. 3, the legs 222a and 232a of the bifurcated fibers are on opposite sides of the filter. Clearly, this need not be the case, and both may be on the same side of the filter, with reflected light traveling along optical fiber 222a to the detector 156.

Figure 4:
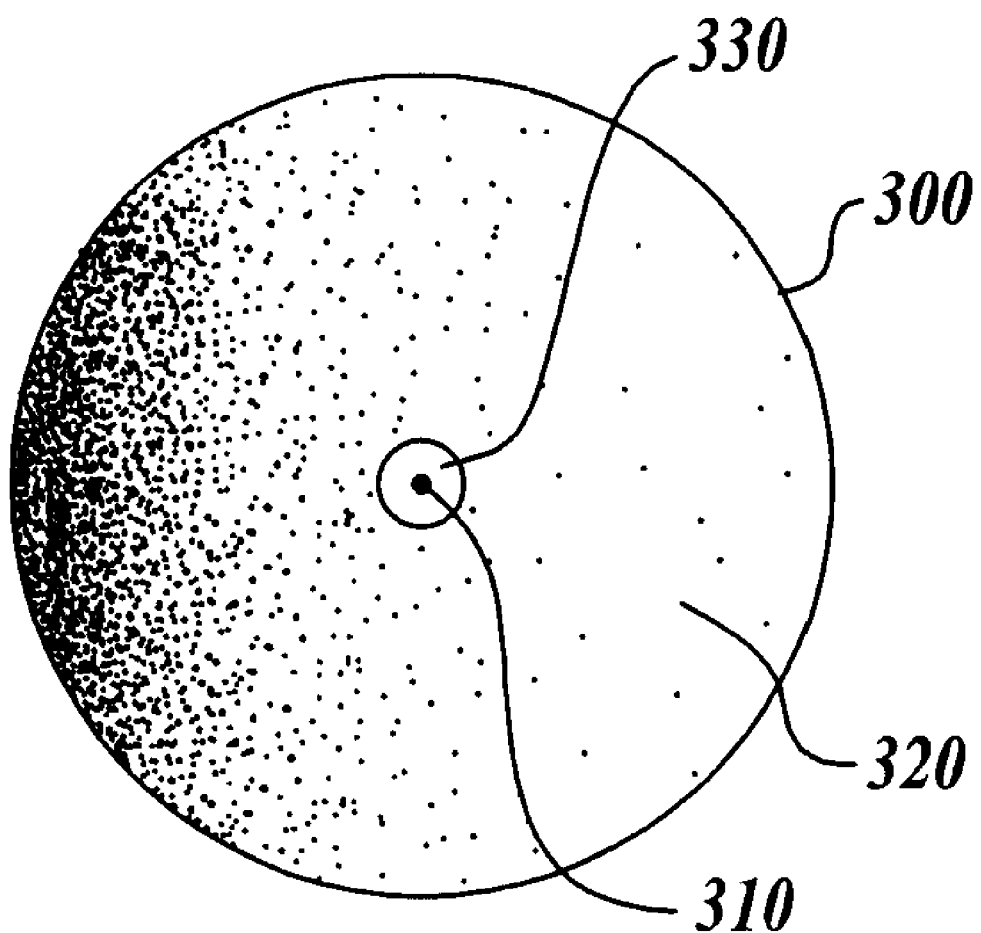
FIG. 4 is a schematic illustration of a planned view of a disk-shaped light filter useful in an embodiment of the invention.
Figure 5:
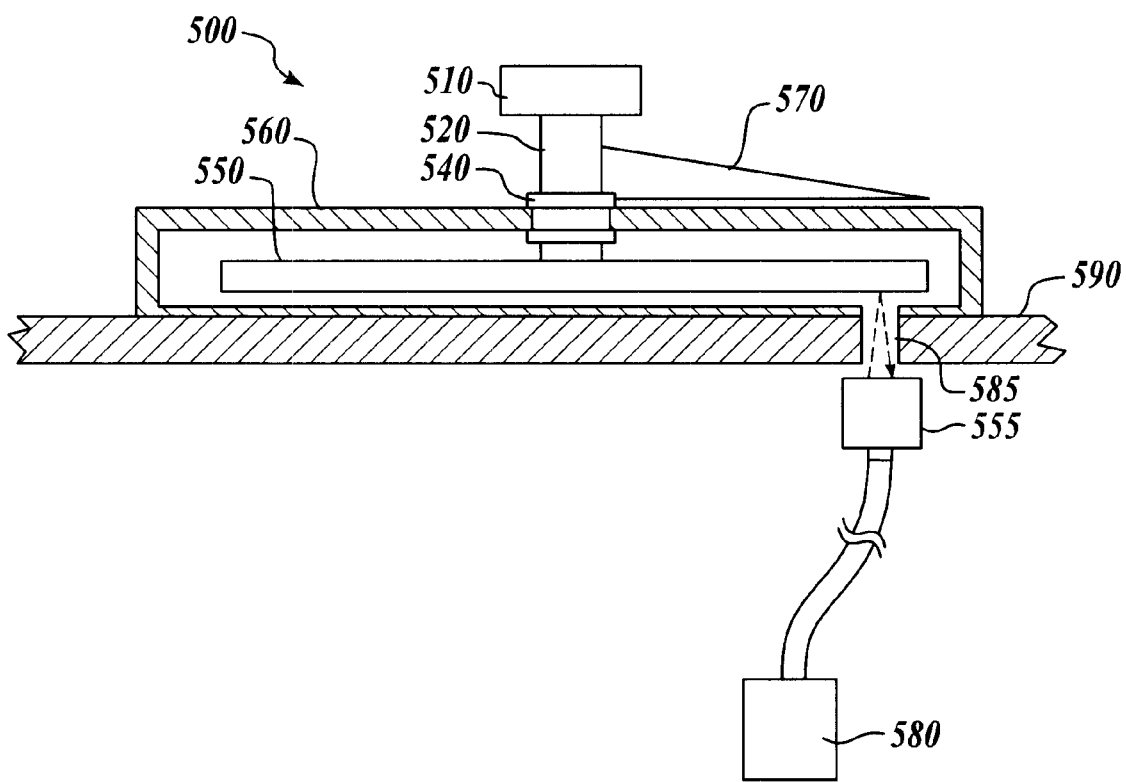
FIG. 5 is a schematic diagram, shown in cross-section, of an embodiment of the invention utilizing the disk-shaped light filter of FIG. 4, to calibrate a spectrometer.

FIG. 4 is a schematic bottom view of an optical calibration disk 300 with a central support shaft 310. The calibration disk has a graduated color reflectance surface 320, and a bottom support bearing 330. This type of disk-shaped reflectance slide is useful in another embodiment of the invention shown in FIG. 5, in cross-sectional side view. The calibration tool 500 has a housing 560 that is light-tight. A disk support shaft 520 extends vertically through the housing 560 with surrounding bearing 540, and has a rotation controller 510 affixed to its upper end. A position pointer 570 extends radially outward from support shaft 520, and sweeps the upper surface of housing 560 when the shaft is rotated. A graduated reflectance disk 550 is mounted, through its center to the lower end of shaft 520, so that the disk rotates in unison with the shaft.

The housing 560, as shown, is aligned on a chemical mechanical polishing pad 590 of a CMP tool (not shown in detail). The polishing pad has a through light path 585, and the end of an optical fiber 555 is aligned with this light path. Thus, light from an optical endpoint sensor 580 can travel through optical fiber 555, and light path 585 to impinge on the disk 550. Light reflected form the disk is carried through optical fiber 555 back to the optical sensor.

As the rotation controller 510 causes the shaft 520 and the disk 550 to rotate, reflectance values corresponding to angular disk position are presented to the optical sensor probe, and disk angular position is identified by the orientation of the position pointer 570 that points to a scale (not shown) with angular measurement attached to the upper surface of the housing 560.

In a preferred embodiment, the graduated reflectance disk has a "spectrum" of reflectance values as a function of angular position around the disk. In other embodiments, the graduated reflectance disk has a thin oxide film deposited on it so that thickness of the film varies with function of angular position. In further embodiments, a thin metal film of tungsten or copper, or another metal, could be deposited so that thickness varies from 0 up to about 100 Ångstroms or thicker as a function of angular position on the disk. Clearly, only a circular band of material is required on the disk, of sufficient width so that the sensor sees the film through the light path 585. A variety of reflectance films and reflectance materials may be chosen without departing from the scope of the invention.

As in the case of other embodiments of this invention, the rotation controller 510 may be computer controlled using a motor and electronic position sensor may be used to determine angular displacement of the disk 550.

Figure 8:
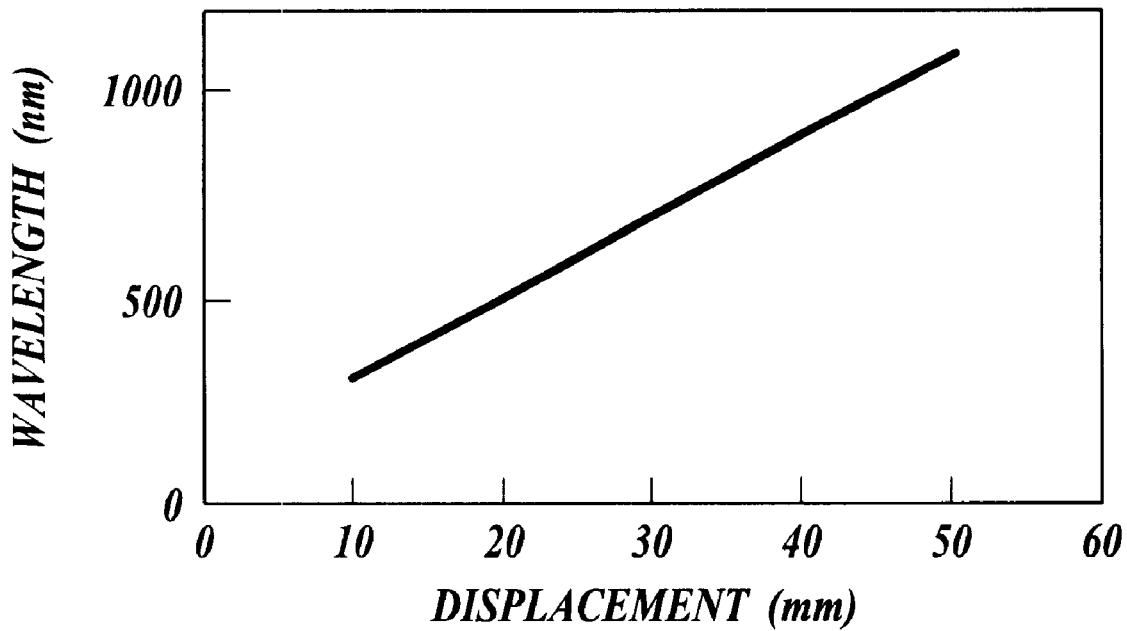
FIG. 8 is a graphical representation of wavelength versus displacement of a calibration slide, useful in understanding a normalization technique of the invention.
Figure 9:
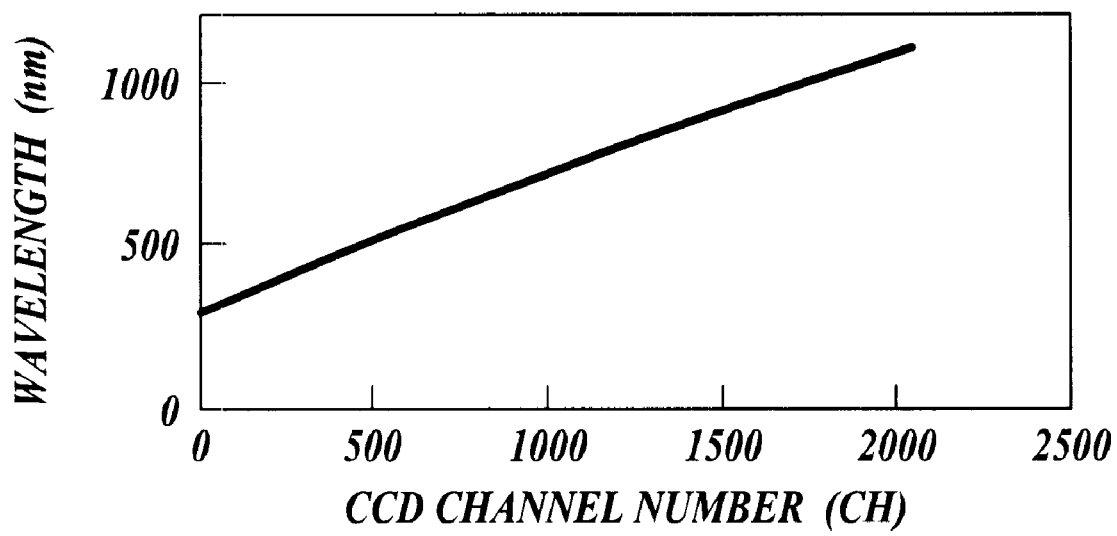
FIG. 9 is a graphical representation of wavelength versus channel number in the detector, useful in understanding a normalization technique of the invention.

With respect to FIGS. 1 and 4, wavelength of light transmitted or reflected from the filter slide varies with displacement along the length of the slide or angular displacement. For the linear slide, this relationship is graphically depicted in FIG. 8, which shows the variation of wavelength $\lambda_t$ with displacement at various points along the slide. The same type of graph can be developed for the disk filter, where the x-axis is angular displacement from o to 360 degrees. Thus one may set the wavelength of the calibration slide by selecting the displacement. FIG. 9 shows the wavelength, $\lambda_{ch}$, vs. channel number in the CCD as measured by a particular spectrometer when using the slide 140 as a wavelength calibration tool. According to the invention, the wavelength as is known from the displacement of the slide vs. channel number in the CCD is used in EQ. 1 to determine the wavelength vs. channel number for the spectrometer.

In accordance with the invention, the slide is set as a "standard" for the wavelength and the corresponding measured values, the channel numbers of the spectrometer are both fed into the calibration equation EQ. 1. Using this technique, unique normalization coefficients can be developed for each spectrometer of a multi-spectrometer facility. Thus, each spectrometer, although it may differ from the others in terms of its "measured" wavelength vs. channel number, should provide the same wavelength reading after normalization.

Clearly, in ordinary use, the spectrometer will detect wavelengths intermediate the points along the wavelength bandwidth that were specifically measured and compared with true wavelengths (from the slide) for normalization. In that event, use is made of equation EQ. 1, and interpolation techniques known to those of skill in the art of mathematics and statistics for wavelengths that are split between adjacent channels in the CCD. Interpolation can use more than two neighboring readings, and may be of the straight-line, polynomial or any other best fit technique.

Calibration for wavelength, in accordance with the invention, may be carried out by inserting one end of the input optical fiber into the optical calibration tool, and the other end of the fiber into the endpoint system light source. Likewise, one end of the output optical fiber is inserted into the calibration tool, and the other end into the endpoint system spectrometer. The optical calibration tool is set so that the fibers are adjacent the 400 nm end of the variable filter, for example the linear filter. The spectrometer system then captures a spectrum. The spectrum is typically from about 400 nm to about 850 nm. The value of the peak wavelength, according to the spectrometer is recorded and compared with the value of the peak wavelength according to the filter, by reading from the screw movement mechanism. These measurements are repeated for at least five different wavelength values, such that a curve similar to the one shown in FIG. 9 can be developed. By comparing the spectrometer readings with the optical calibration instrument readings, an average wavelength error can be calculated. If the error is less then a predetermined value, then the calibration of the spectrometer is within acceptable limits. If not, the spectrometer should be recalibrated using the data just gathered.

In a similar way, in accordance with the invention, light intensity vs. wavelength is also normalized for each spectrometer of a multi-spectrometer facility. In this case, a standard light source is used and its intensity is compared with intensity readings of the spectrometer, and the spectrometer readings are normalized to that of the standard light source, following a similar proceeding to that for wavelength normalization. For example, a standard light source such as the LS-1 from Ocean Optics, Inc., Dunedin, Fla., may be used in conjunction with a neutral density filter to attenuate the overall light output. Several neutral density filters are available, for example that available from Edmund Scientific Company, Barrington, N.J. Light is transmitted from the standard source and neutral density filter through the filter slide to a fiber optic meter-head, such as that obtainable from Fluke Corporation, a wholly owned subsidiary of Danaher Corporation, Washington, D.C. The recorded intensity vs. wavelength, at several pre-selected wavelengths, is then used as a local standard for all of the spectrometers to be calibrated. The optic meter-head is used to verify that the standard light is within specifications, and to determine and record the relative intensity vs. wavelength through the filter slide to form a local standard. The spectrometer replaces the meter-head and the fiber optic cable is removed from the standard light source, and hooked up to the light source on the test, that will ordinarily be used when the spectrometer is in service. The intensity vs. wavelength at the pre-selected frequencies is then recorded for the combination of the light source to be used in normal operation and the spectrometer to be used for the light source. Comparison of these results to those obtained with the standard light source and the meter-head allows one to "normalize" the combination to a local standard. This operation performed for each of the combination light source and spectrometer will ensure that all systems in operation will produce the same measured spectrum given the same sample to measure.

Figure 10:
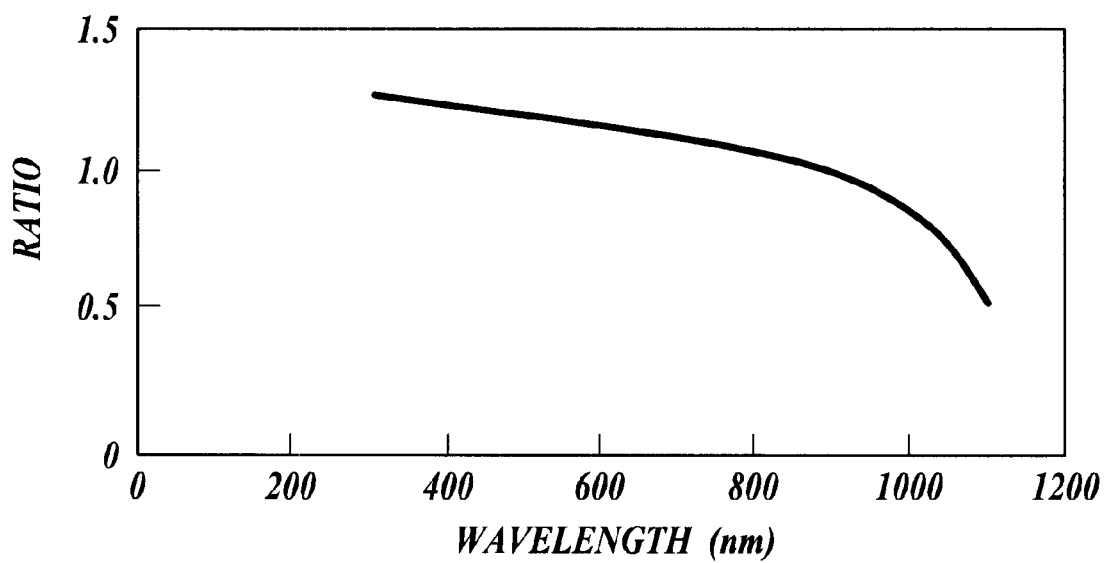
FIG. 10 is an illustration of the comparison between the spectrum from the standard source and meter-head to the spectrum from the source and spectrometer that ordinarily will be used during service.

FIG. 10 is an illustration of the comparison (shown as the ratio) between the spectrum from the standard source and meter-head to the spectrum from the local source and spectrometer, $Im_\lambda$, that ordinarily will be used during service. It is also good practice to verify that the light source that the spectrometer will ordinarily use meets spectral and intensity requirements. It is recommended that each reading of this intensity calibration be repeated several times to ensure a sufficient number of data points for subsequent reliable normalization of intensity from the light source to the intensity from the standard light source that will be the "standard" to which each of the spectrometers will be normalized. A calibration for intensity may be represented as shown in EQ. 2.

$$R_\lambda = B_0 + (B_1 * \lambda) + (B_2 * \lambda * \lambda) + (B_3 * \lambda * \lambda) \qquad (EQ.2)$$

Where:

$R_\lambda$=the ratio of intensity of the measured spectrum from the local standard light source and meter-head to the measured intensity from the light source and spectrometer combination to be used in the operating system at wavelength $\lambda$ (the normalizing vector)

$B_0$=the intensity of the measured spectrum calibration offset $B_1$=$1^{st}$ coefficient (I/nm)

$B_2$=$2^{nd}$ coefficient (I/nm$^2$)

$B_3$=3rd coefficient (I/nm$^3$)

$\lambda$=the wavelength in nanometers (nm)

These coefficients must be determined fairly frequently if the calibration of the spectrometer is to be maintained and if the results of one spectrometer are to be compared to another.

Hence the standardized spectrum from a light source and spectrometer may be calculated by EQ. 3

$$I_\lambda = R_\lambda * Im_\lambda \qquad (EQ. 3)$$

Where:

$I_\lambda$=the calibrated and normalized intensity at wavelength $\lambda$ $R_\lambda$=the calibration vector from EQ. 2

$Im_\lambda$=the measured spectrum, before normalization for intensity but corrected for wavelength, from the local source and spectrometer, $Im_\lambda$, that ordinarily will be used during service.

Figure 6:
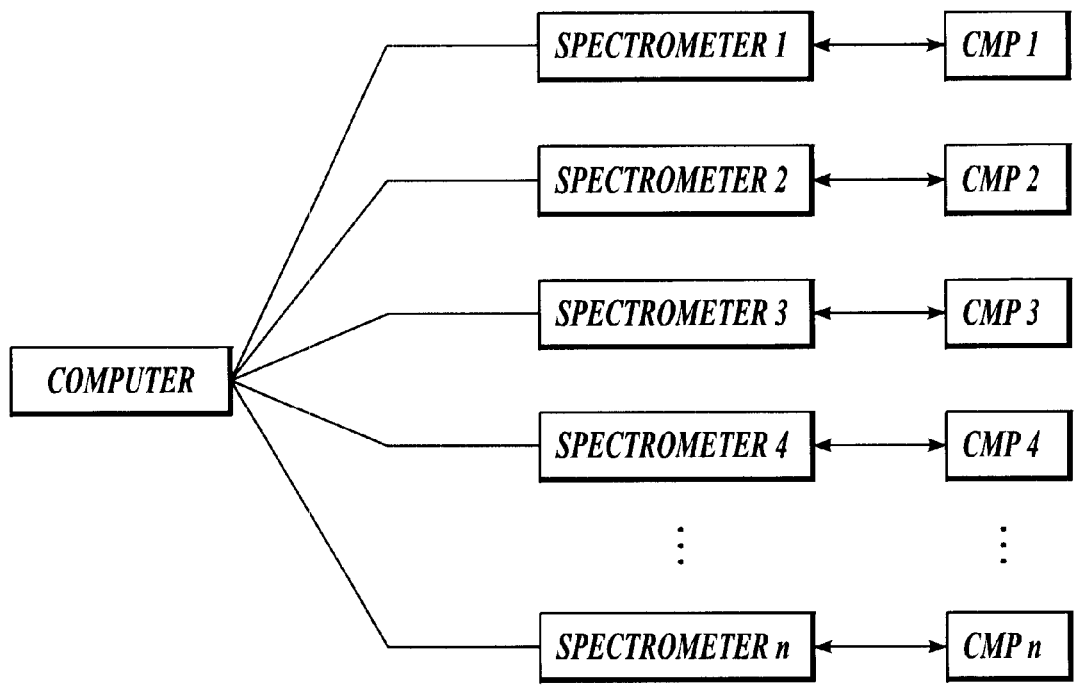
FIG. 6 is an embodiment of an arrangement of spectrometers in a multi-spectrometer arrangement in accordance with the invention.

There are a variety of possible permutations for using spectrometers in a multi-spectrometer facility, such as a fab, using CMP. One such arrangement is shown in FIG. 6. In this arrangement, each CMP machine has a separate spectrometer, and these spectrometers are each in communication with a common computer. The information regarding the test standard polished wafer is stored in the computer and each spectrometer is able to access that information and compare it with spectral information obtained from online monitoring of the surface of wafers being polished. This is a significant departure from the prior art, where each of the spectrometers would be individually calibrated to a separate standard test wafer, and the group of spectrometers would not be able to use a common standard test wafer spectral signature stored on the computer to reliably detect endpoint.

Figure 7:
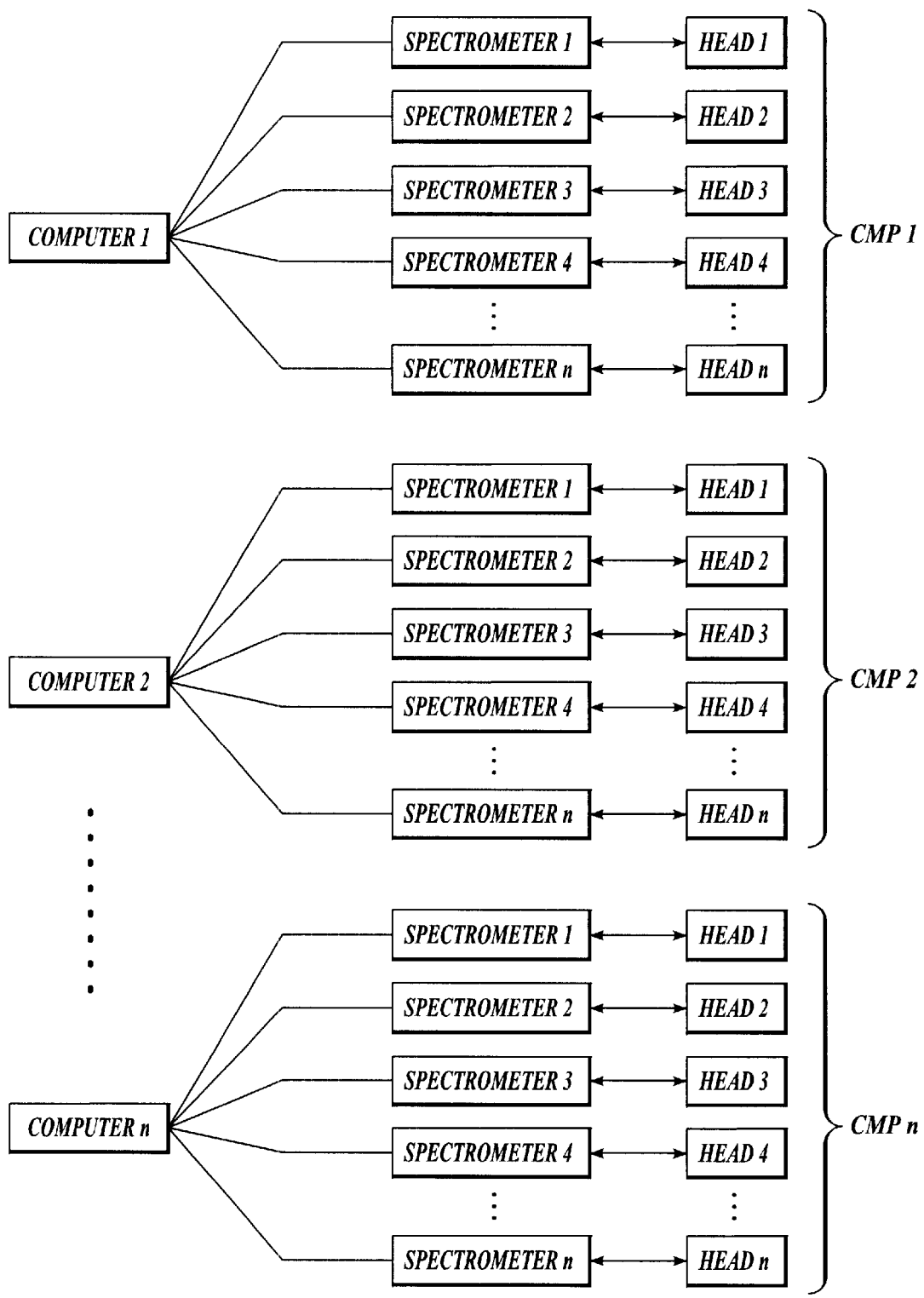
FIG. 7 is another embodiment of an arrangement of spectrometers in a multi-spectrometer facility, in accordance with the invention.

An alternative arrangement of spectrometers in a multi-spectrometer fab environment is shown in FIG. 7. In this environment, each CMP machine has several heads for polishing semiconductor wafers. Each head may have the capability to polish several wafers simultaneously. Each head is supplied with a separate spectrometer, thus there are as many spectrometers as there are heads for each CMP machine. Each CMP machine in the arrangement shown in FIG. 7 has a separate computer, and all of the spectrometers of each CMP machine are in communication with the computer associated with that particular machine. Once again, in accordance with the invention, a common normalized standard test wafer spectral signature is stored in the computer, and each of the spectrometers associated with a particular CMP machine is able to access the spectral signature for comparison with the normalized spectral signatures of wafers being polished in order to detect or predict the endpoint reliably. This differs from an arrangement in which each of the spectrometers has a separate standard test wafer signature, which it uniquely accesses, and uses to detect the endpoint for wafers that it is monitoring.

The foregoing description provides an enabling disclosure of the invention, which is not limited by the description but only by the scope of the appended claims. All those other aspects of the invention that will become apparent to a person of skill in the art, who has read the foregoing, are within the scope of the invention and of the claims herebelow.

We claim:

1. A method of calibrating a spectrometer comprising:
   selecting a filter slide having a predetermined light transmittance and reflectance variation with location on the slide;
   causing light from a light source to be incident upon selective portions of the filter, the portions each transmitting and reflecting light at a predetermined wavelength;
   receiving transmitted light from the filter portions at a receiver of a spectrometer; and
   calibrating from the spectrometer using actual spectrometer readings of the received light and corresponding predetermined wavelengths based on filter slide displacement.

2. The method of claim 1, wherein the filter slide comprises a linear filter slide wherein transmittance varies with linear displacement along a length of the slide.

3. The method of claim 1, wherein the filter slide comprises a circular filter slide wherein transmittance varies with angular displacement.

4. The method of claim 1, wherein the causing of light to be incident on the filter comprises aligning an output optical fiber on one side of the filter and an input optical fiber on another side of the filter.

5. The method of claim 1, wherein the causing light to be incident on the filter comprises aligning an output optical fiber and an input optical fiber on a common side of the filter.

6. The method of claim 1, wherein the causing light to be incident on the filter comprises transmitting light through the filter, and the receiving comprises receiving light transmitted through the filter.

7. The method of claim 1, wherein causing light to be incident on the filter comprises reflecting light from a surface of the filter, and the receiving of light comprises receiving reflected light.

8. The method of claim 1, wherein the calibrating comprises:
comparing a series of measured wavelengths to a corresponding series of wavelengths determined from the filter slide;
calculating normalization coefficients for each of the measured and corresponding wavelengths, the coefficients derived from the formula:

$$\lambda_{ch}=C_0+(C_1*ch)+(C_2*ch*ch)+(C_3*ch*ch*ch) \quad (EQ.1)$$

Where:
$\lambda_{ch}$=wavelength in nanometers (nm) of channel number (ch) in the CCD
$C_0$=wavelength of channel number zero (0)
$C_1$=$1^{st}$ coefficient (nm/ch)
$C_2$=$2^{nd}$ coefficient (nm/ch$^2$)
$C_3$=3rd coefficient (nm/ch$^3$)
ch=channel number in the CCD.

9. The method of claim 8, wherein the calibrating further comprises measuring light intensity at a series of discrete wavelengths and comparing measured intensity with standard intensity from a standard source for light intensity; and normalizing measured intensity to standard intensity at each of the series of wavelengths.

10. The method of claim 8, further comprising calibrating the spectrometer for comprising light intensity vs. wavelength using the formulae:

$$R_\lambda=B_0+(B_1*\lambda)+(B_2*\lambda*\lambda)+(B_3*\lambda*\lambda*\lambda) \quad (EQ.2)$$

Where:
$R_\lambda$=the ratio of intensity of the measured spectrum from the local standard light source and meter-head to the measured intensity from the light source and spectrometer combination to be used in the operating system at wavelength $\lambda$ (the normalizing vector)
$B_0$=the intensity of the measured spectrum calibration offset
$B_1$=$1^{st}$ coefficient (I/nm)
$B_2$=$2^{nd}$ coefficient (I/nm$^2$)
$B_3$=3rd coefficient (I/nm$^3$)
$\lambda$=the wavelength in nanometers (nm); and:

$$I_\lambda=R_\lambda*Im_\lambda \quad (EQ.3)$$

Where:
$I_\lambda$=the calibrated and normalized intensity at wavelength $\lambda$
$R_\lambda$=the calibration vector from EQ. 2
$Im\lambda$=the measured spectrum, before normalization for intensity but corrected for wavelength, from the local source and spectrometer, $Im_\lambda$.

11. The method of claim 1, further comprising calibrating the spectrometer for light intensity vs. wavelength using the formulae:

$$R_\lambda=B_0+(B_1*\lambda)+(B_2*\lambda*\lambda)+(B_3*\lambda*\lambda*\lambda) \quad (EQ.2)$$

Where:
$R_\lambda$=the ratio of intensity of the measured spectrum from the local standard light source and meter-head to the measured intensity from the light source and spectrometer combination to be used in the operating system at wavelength $\lambda$ (the normalizing vector)
$B_0$=the intensity of the measured spectrum calibration offset
$B_1$=$1^{st}$ coefficient (I/nm)
$B_2$=$2^{nd}$ coefficient (I/nm$^2$)
$B_3$=3rd coefficient (I/nm$^3$)
$\lambda$=the wavelength in nanometers (nm); and $$I_\lambda=R_\lambda*Im_\lambda \quad (EQ.3)$$

Where:
$I_\lambda$=the calibrated and normalized intensity at wavelength $\lambda$
$R_\lambda$=the calibration vector from EQ. 2
$Im\lambda$=the measured spectrum, before normalization for intensity but corrected for wavelength, from the local source and spectrometer, $Im_\lambda$.

12. A system comprising a plurality of spectrometers, the system comprising:
(a) spectrometers calibrated by normalization of measured input light wavelength and intensity information to standard wavelength and intensity information of the input light;
(b) at least one computer in communication with the spectrometers, the computer accessing memory comprising spectral information, in digitized form, relating to a test workpiece, the computer comparing spectral information communicated from the spectrometers, after normalization, to the stored spectral information to determine a degree of difference between the stored and communicated information.

13. The system of claim 12, wherein the normalization comprises:
comparing measured light wavelengths of each of the spectrometers with actual wavelengths for the light at at least n different wavelengths, and determining normalization coefficients derived from the formula:

$$\lambda_{ch}=C_0+(C_1*ch)+(C_2*ch*ch)+(C_3*ch*ch*ch) \quad (EQ.1)$$

Where:
$\lambda_{ch}$=wavelength in nanometers (nm) of channel number (ch) in the CCD
$C_0$=wavelength of channel number zero (0)
$C_1$=$1^{st}$ coefficient (nm/ch)
$C_2$=$2^{nd}$ coefficient (nm/ch$^2$)
$C_3$=3rd coefficient (nm/ch$^3$)
ch=channel number in the CCD.

14. The system of claim 13, wherein the test piece comprises a semiconductor wafer, and the stored spectral information comprises information obtained from optically monitoring a semiconductor wafer film while the film is being polished.

15. The system of claim 13, further comprising determining an endpoint with the comparing of the communicated spectral information with stored spectral information yields a predetermined degree of difference.

16. The system of claim 13, further comprising calibrating the spectrometer for light intensity vs. wavelength using the formulae:

$$R_\lambda=B_0+(B_1*\lambda)+(B_2*\lambda*\lambda)+(B_3*\lambda*\lambda*\lambda) \quad (EQ.2)$$

Where:
$R_\lambda$=the ratio of intensity of the measured spectrum from the local standard light source and meter-head to the measured intensity from the light source and spectrometer combination to be used in the operating system at wavelength λ (the normalizing vector)

$B_0$=the intensity of the measured spectrum calibration offset $B_1$=1$^{st}$ coefficient (I/nm)

$B_2$=2$^{nd}$ coefficient (I/nm$^2$)

$B_3$=3rd coefficient (I/nm$^3$)

λ=the wavelength in nanometers (nm); and $$I_\lambda = R_\lambda * Im_\lambda \qquad (EQ. 3)$$

Where:

$I_\lambda$=the calibrated and normalized intensity at wavelength λ

$R_\lambda$=the calibration vector from EQ. 2

Imλ=the measured spectrum, before normalization for intensity but corrected for wavelength, from the local source and spectrometer, $Im_\lambda$.

17. The system of claim 12, wherein the test piece comprises a semiconductor wafer, and the stored spectral information comprises information obtained from optically monitoring a semiconductor wafer film while the film is being polished.

18. The system of claim 17, wherein the spectral information comprises information sufficient to determine or predict an endpoint for polishing the film.

19. The system of claim 17, further comprising determining an endpoint with the comparing of the communicated spectral information with stored spectral information yields a predetermined degree of difference.

20. The method of claim 12, further comprising determining an endpoint with the comparing of the communicated spectral information with stored spectral information yields a predetermined degree of difference.

21. The system of claim 12, wherein each spectrometer is in communication with a separate computer.

22. The system of claim 12, wherein groups of spectrometers selected from the plurality of spectrometers are in communication with a common computer.

23. The system of claim 22, wherein each spectrometer monitors a single polishing head of a chemical mechanical polishing tool.

24. The system of claim 22, wherein each group of spectrometers monitors a chemical mechanical polishing tool, each group of spectrometers comprising as many spectrometers as a number of heads of the chemical mechanical tool with which the group of spectrometers is associated.

25. The system of claim 12, further comprising a plurality of spectrometers, the system comprising:

(a) spectrometers calibrated by normalization of measured input light wavelength and intensity information to standard wavelength and intensity information of the input light;

(b) at least one computer in communication with the spectrometers, the computer accessing memory comprising stored spectral information, in digitized form, relating to a test workpiece, the computer comparing spectral information communicated from the spectrometers, after normalization, to the stored spectral information to determine a degree of difference between the stored and communicated information.

26. An apparatus for calibrating a spectrometer, the apparatus comprising:

a light source transmitting light via an input optical fiber;

a detector receiving light signals via an output optical fiber; and a filter slide having a predetermined light transmittance or reflectance at locations on the slide;

wherein light from the light source is incident upon the slide and light reflected or transmitted from the filter communicated to the detector via the output optical fiber.

27. The apparatus of claim 26, wherein the input optical fiber and the output optical fiber are each bifurcated optical fibers, one leg of the bifurcated input optical fiber in direct optical communication with a leg of the bifurcated output optical fiber.

28. The apparatus of claim 26, wherein the filter slide comprises a lengthwise dimension, and light transmittance varies with displacement along the length of the slide.

29. The apparatus of claim 26, wherein the filter slide comprises an angular dimension, and light transmittance varies with angular displacement on the slide.

30. The apparatus of claim 26, wherein the input fiber optic cable and the output fiber optic cable each have respective ends, and the respective ends are directed to opposite sides of the filter slide so that light exiting the end of the input optical fiber is communicated through the filter slide to the end of the output optical fiber.

31. The apparatus of claim 26, further comprising:

a computer, the computer comprising memory and a processing unit, the memory storing spectral data comprising light wavelength measured at the detector when light is incident on locations on the slide, and corresponding predetermined wavelengths based on the locations of the slide whereupon light is incident.

32. The apparatus of claim 31, wherein the processing unit calculates normalization coefficients to normalize each measured wavelength to a corresponding predetermined wavelength.

33. A system for calibrating a spectrometer, the system comprising:

a standard light source of known intensity;

a neutral light filter;

a test light source used in association with the spectrometer in monitoring optical properties of a workpiece;

fiber optic cable, the cable releasably connectable to the test and standard light sources, and the spectrometer; and a computer;

wherein, during calibration, light from the standard light source is transmitted through the filter to the spectrometer for light intensity measurement and recordal; separately light from the test light source is transmitted via the cable to the spectrometer for measurement and recordal; and the computer is configured to normalize measured light intensity from the test light source to the standard light source using the formulae:

$$R_\lambda = B_0 + (B_1*\lambda) + (B_2*\lambda*\lambda) + (B_3*\lambda*\lambda*\lambda) \qquad (EQ.2)$$

Where:

$R_\lambda$=the ratio of intensity of the measured spectrum from the local standard light source and meter-head to the measured intensity from the light source and spectrometer combination to be used in the operating system at wavelength λ (the normalizing vector)

$B_0$=the intensity of the measured spectrum calibration offset
$B_1$=$1^{st}$ coefficient (I/nm)
$B_2$=$2^{nd}$ coefficient (I/nm$^2$)
$B_3$=3rd coefficient (I/nm$^3$)
$\lambda$=the wavelength in nanometers (nm); and:

$$I_\lambda = R_\lambda * Im\lambda \quad (EQ.\ 3)$$

Where:

$I_\lambda$=the calibrated and normalized intensity at wavelength $\lambda$ $R_\lambda$=the calibration vector from EQ. 2

$Im\lambda$=the measured spectrum, before normalization for intensity but corrected for wavelength, from the local source and spectrometer, $Im_\lambda$.

* * * * *